US010245009B2

(12) United States Patent
Miller et al.

(10) Patent No.: US 10,245,009 B2
(45) Date of Patent: Apr. 2, 2019

(54) APPARATUS FOR SAFELY AND ACCURATELY EXCISING CORE TISSUE SAMPLES FROM PALPATED NODULES OR SURFACE LESIONS

(71) Applicants: Stephen Henry Miller, Naples, FL (US); Jonathan Keith Jay, Naples, FL (US)

(72) Inventors: Stephen Henry Miller, Naples, FL (US); Jonathan Keith Jay, Naples, FL (US)

(73) Assignees: Stephen Henry Miller, Naples, FL (US); Jonathan Keith Jay, Naples, FL (US)

( * ) Notice: Subject to any disclaimer, the term of this patent is extended or adjusted under 35 U.S.C. 154(b) by 670 days.

(21) Appl. No.: 14/756,173

(22) Filed: Aug. 11, 2015

(65) Prior Publication Data
US 2016/0058430 A1    Mar. 3, 2016

Related U.S. Application Data

(60) Provisional application No. 62/070,482, filed on Aug. 26, 2014.

(51) Int. Cl.
*A61B 10/02* (2006.01)
*A61B 90/00* (2016.01)
*A61B 17/34* (2006.01)

(52) U.S. Cl.
CPC ...... *A61B 10/0241* (2013.01); *A61B 10/0233* (2013.01); *A61B 2010/0208* (2013.01);
(Continued)

(58) Field of Classification Search
CPC .... A61B 10/04; A61B 10/02; A61B 2090/036
See application file for complete search history.

(56) References Cited

U.S. PATENT DOCUMENTS

| 4,555,243 A * | 11/1985 | Markham | ......... A61B 10/0241 |
| | | | 128/DIG. 26 |
| 4,600,014 A | 7/1986 | Beraha | |

(Continued)

*Primary Examiner* — Daniel L Cerioni
*Assistant Examiner* — Yasmeen S Warsi
(74) *Attorney, Agent, or Firm* — Dickinson Wright PLLC

(57) ABSTRACT

Apparatus for safely and accurately positioning the fingertip of a physician (or technician) performing a biopsy procedure, e.g., to excise a core tissue samples of the male prostate or other internal organs, to avoid injury (e.g., a needle stick) from the sharpened distal end of a biopsy needle assembly. Such apparatus comprises an open tubular member defining an elongated passageway through which a biopsy needle assembly, when actuated, can be made to pass and to extend a predetermined distance along an external path in order to effect the core sampling of a biological mass of interest. The tubular housing supports a safety flange at its distal end, such flange having a flat surface adapted to be engaged by the fingertip of the physician prior to actuation of the biopsy needle assembly. Preferably, the engaged surface of the safety flange defines a physical fiducial adapted to be sensed by the user's fingertip, such fiducial being located a predetermined safe distance from the external path traveled by the needle assembly, whereby the physician is assured that his or her fingertip is safely spaced from the needle assembly when actuated, and the distal end of the tubular housing is precisely positioned relative to a biological mass of interest.

9 Claims, 5 Drawing Sheets

Fig. 5

(52) U.S. Cl.
CPC . *A61B 2017/3405* (2013.01); *A61B 2090/034* (2016.02); *A61B 2090/036* (2016.02); *A61B 2090/0801* (2016.02)

(56) References Cited

U.S. PATENT DOCUMENTS

| | | | |
|---|---|---|---|
| 4,776,346 A | | 10/1988 | Beraha |
| 4,943,295 A | * | 7/1990 | Hartlaub ............ A61B 17/3211 30/329 |
| 5,555,892 A | * | 9/1996 | Tipton ................... A61B 10/02 600/564 |

* cited by examiner

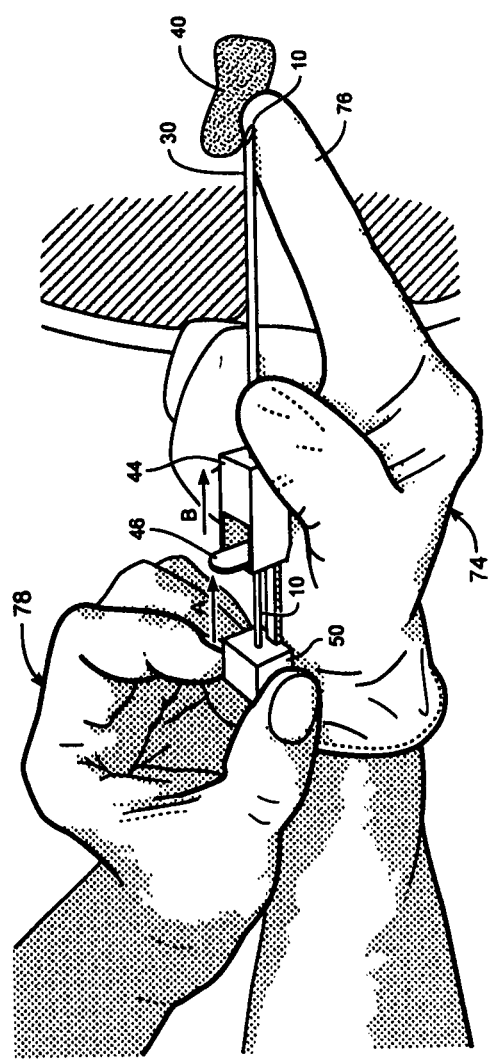
Fig. 1- PRIOR ART

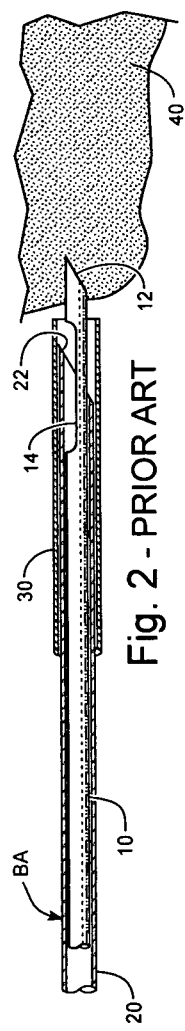
Fig. 2 - PRIOR ART
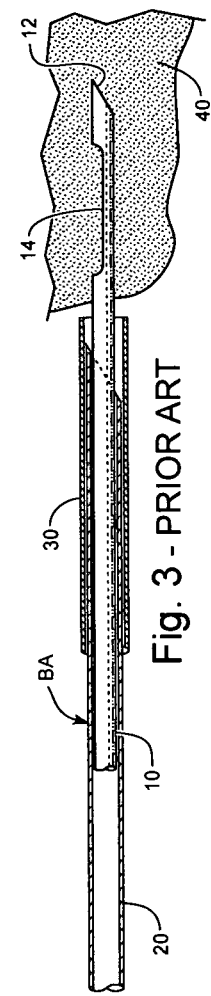
Fig. 3 - PRIOR ART
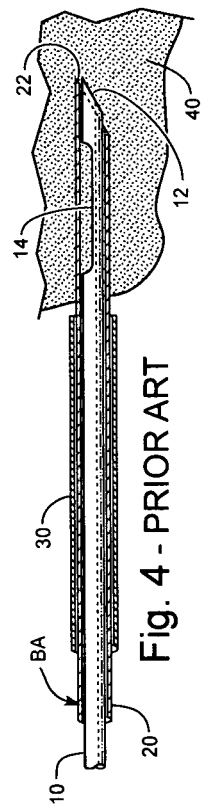
Fig. 4 - PRIOR ART

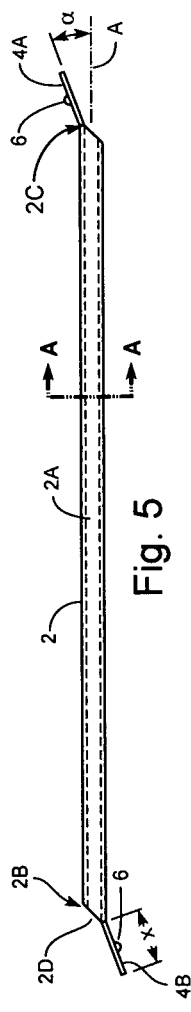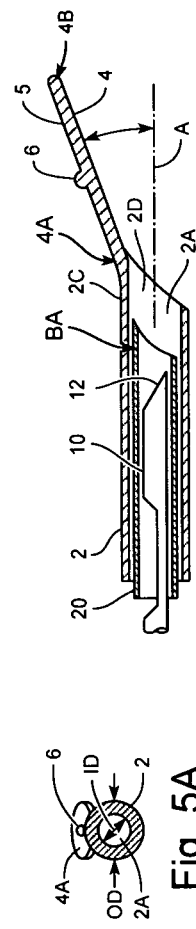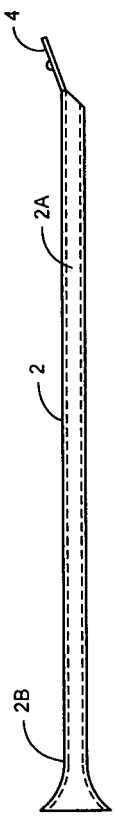

APPARATUS FOR SAFELY AND ACCURATELY EXCISING CORE TISSUE SAMPLES FROM PALPATED NODULES OR SURFACE LESIONS

CROSS REFERENCE TO RELATED APPLICATIONS

This application claims priority from U.S. Provisional Application No. 62/070,482, filed on Aug. 26, 2014, and entitled "Apparatus for Safely and Accurately Excising Core Tissue Samples from Palpated Nodules or Surface Lesions," the disclosure of which is incorporated herein, in its entirety, by reference.

BACKGROUND OF THE INVENTION

Field of the Invention

The present invention relates to improvements in apparatus for taking core tissue samples of, for example, the male prostate or other internal organs at locations corresponding to surface irregularities that can be palpated by the fingertip of a physician (or technician). More specifically, it relates to apparatus for decreasing the risk of finger puncture and improving the accuracy of the biopsy of lesions of interest.

Discussion of the Prior Art

During routine digital examination of the prostate, it is common for the examiner to use his or her fingertip to probe the initial 10 centimeters or so of the rectum to detect any suspicious surface irregularities (e.g., lesions or nodules) that can be felt on the inner surface of the rectal wall or the outer surface of the prostate gland. Having manually palpated irregularities on or through the wall of the rectum, it is often desirable to take a core biopsy of one or more areas of these lesions for subsequent analysis.

In biopsying the irregularities noted above, it is essential that the examining person accurately position the biopsy needle onto a irregularity of interest. It is also essential to accurately position the palpating fingertip out of "harm's way" at the time the biopsy is performed. A "needle stick' is not only painful to the recipient, but it also can result in the transmission of serious diseases to the examiner biopsying the lesion. To achieve this accuracy during the biopsy procedure, the examiner must simultaneously maintain the position between his or her palpating fingertip and the irregularity of interest, while maneuvering the free end of a biopsy needle assembly to a position closely spaced from the palpating fingertip. Having done so, the physician then activates a triggering mechanism that causes the biopsy needle to quickly reciprocate in axial directions, first moving in a direction to penetrate the irregularity to excise a core sample therefrom, and then moving in an opposite direction in which the needle is withdrawn from the sample and returned to its sheath.

In taking tissue samples as described above, it will be appreciated that the physician must be exceedingly careful to avoid being accidentally injured by the tip of the biopsy needle. Since, at the time of taking the sample, neither the mass of interest nor the tip of the biopsy needle can be visualized, the physician must rely on his or her sense of touch to assure the accuracy of the procedure and his or her safety in performing the procedure. The prospect of an accidental needle stick is exacerbated by the need to position both the needle tip and the palpating fingertip as close as possible to the lesion of interest at the time the biopsy is taken. Generally, the closer this spacing, the higher the accuracy of the biopsy and, unfortunately, the greater the risk of an accidental finger stick by the needle.

The above-noted close spacing among a palpating fingertip, the tip of a biopsy needle and an irregularity of interest will be appreciated from the prior art drawings of FIGS. 1-4 hereof. These drawings have been taken from U.S. Pat. No. 4,600,014 to Beraha. This patent publication discloses a relatively early mechanical device for taking core samples of a prostate gland 40. As shown, the device includes a handle 44 portion designed to be held in the palm of a physician's gloved right hand 74 during the biopsy procedure. Forwardly extending from, and rigidly mounted to the handle, is an elongated, relatively rigid guide tube 30 having a slidably-mounted cannula 20 therein. The latter typically comprises a hollow stainless steel tube 21 having a sharpened distal end 22. As shown in FIGS. 2-4, cannula 20 slidably supports an internal tissue-sampling stylet 10 having a sharpened distal end 12. Together with cannula 20, stylet 10 defines a biopsy assembly BA.

As noted above, cannula 20 is axially movable within the guide tube 30, and its axial position is controlled by the position of a manually movable tab 46 that is slidably-mounted on the handle 44 and rigidly connected to the cannula. Axial movement of the stylet 10 within the cannula 20 is controlled by a knob 50 that is also slidably mounted on the handle 40. As best shown in FIG. 3, a transverse sampling slot 14 is formed in the stylet wall near the sharpened distal end of the stylet. In use, when knob 50 is moved forwardly, the sharpened end 12 of the stylet will project forwardly of the cannula end 22 to a position in which it may be is inserted into the prostate. When so positioned, a portion of the prostate tissue displaced by the stylet will fill the slot 14. At this time, forward movement of tab 46 will cause the sharpened distal end cannula 20 to slice through the prostate and isolate that portion of the prostate located within slot 14 of the stylet. The isolated portion of the prostate within slot 14 constitutes the core sample of interest. Having taken the core sample, the cannula and its internal stylet are then withdrawn from the prostate and returned to the guide tube 30.

According to the disclosure of the above-noted patent, the apparatus disclosed is used as follows: Referring to FIG. 1, the physician first places the handle 40 in the palm of the right hand with the thumb tab 46 facing outward. Prior to this, the needle assembly is loaded into the guide tube so that, while the sharpened distal end of the cannula does not extend beyond the distal end of the guide tube, the sharpened distal end of the stylet extends slightly beyond the guide tube end. This configuration is shown in FIG. 2. The tip of the index finger 76 is then placed at the distal end of the guide tube 30, and the stylet 10 is moved to a position in which its sharpened tip 12 is "forced" against the physician's fingertip. Using the right hand only, the physician inserts the index finger and guide tube 30 into the patient's rectum and contacts the prostate gland. The physician then palpates the gland to locate a suspicious surface irregularity. (In doing this, it is assumed that the physician releases contact between the fingertip and the sharpened stylet tip. Having located an irregularity of interest, the physician will then force the protruding distal end of the stylet into the irregularity, as shown in FIG. 2 and then advance tab 46 forwardly to cause a desired penetration of the of the stylet into the prostate, e.g., to an extent shown in FIG. 3. Then, the physician uses the left hand 78 to push knob 50 forwardly, thereby causing the sharpened end cannula 20 slice through the prostate to capture the core sample in the transverse slot 14 of the stylet. See FIG. 4.

From the foregoing, it will be appreciated that there may be significant safety issues in using the apparatus described. For example, the suggested initial creation of a contact "force" between the physician's fingertip and the stylet tip may well cause a needle stick even before the apparatus is inserted into the rectum. Further, upon removing the fingertip from the sharpened end of the stylet in order to explore (i.e., palpate) the surface of the prostate, an uncertainty is created between the respective positions of the fingertip and the sharpened stylet tip. In such case, movement of the stylet tip to penetrate a nodule of interest without knowing exactly where the fingertip is located may also cause a needle stick of the physician's fingertip. Also, because of this uncertainty, the accuracy of the biopsy may be compromised, causing an unintended portion of the prostate to be biopsied.

SUMMARY OF THE INVENTION

In view of the foregoing, an object of this invention is to provide a safer and more accurate apparatus for excising a core sample from a palpatable internal lesion for subsequent analysis.

According to a preferred embodiment of the invention, apparatus that achieves the above objective comprises an elongated hollow tubular housing having opposing proximal and distal ends. This tubular housing, which is adapted to be hand-held by a person performing a biopsy procedure, defines an open longitudinal passageway extending between the opposing ends of the tubular housing. The passageway is adapted (i) to slidably receive a biopsy needle assembly inserted into the passageway at the proximal end of the tubular member, and (ii) to guide the biopsy needle assembly through the passageway until a portion of the needle assembly exits from the passageway and extends a predetermined distance from the distal end of the housing in order to excise a core sample of interest. Mounted on the distal end of the tubular housing at a location proximate that location where the needle assembly exits from the passageway is a rigid safety flange member that extends at an acute angle away from the longitudinal axis of the passageway. This flange member is adapted to be engaged by the fingertip of the user at the time the biopsy needle assembly is actuated for the purpose of biopsying a sample. Owing to its location, the flange member shields the fingertip from contact with the needle assembly as the latter is moved axially to biopsy the sample. Preferably, the flange member defines a fiducial that is readily sensed by the fingertip, whereby (a) the fingertip is precisely positioned on the flange member to prevent a needle stick during the biopsy procedure, and (b) the needle tip accurately enters the lesion the interest.

The invention and its advantages will be better understood from the ensuing detailed description of preferred embodiments, reference being made to the accompanying drawings wherein like reference characters denote like parts.

BRIEF DESCRIPTION OF THE DRAWINGS

FIG. 1 illustrates a known apparatus for taking a core sample of a prostate gland;

FIGS. 2-4 illustrate the movement of the major components of a conventional biopsy needle assembly used in the FIG. 1 apparatus;

FIGS. 5 and 6 are side and top plan views of a preferred embodiment of the invention;

FIG. 5A is an enlarged cross-sectional view of the FIG. 5 apparatus taken along the section line A-A;

FIG. 7 is an enlarged cross-sectional illustration of the distal end portion of the FIG. 5 apparatus, showing a portion of a biopsy needle assembly therein;

FIG. 9 is a side elevation of an alternate embodiment of the invention.

DETAILED DESCRIPTION OF PREFERRED EMBODIMENTS

Figure 8A:
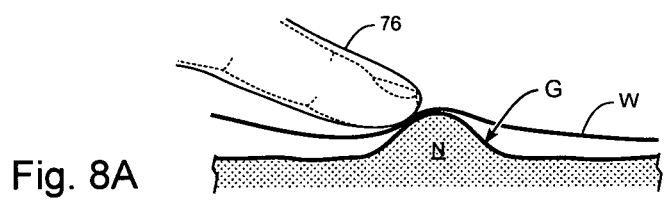
FIGS. 8A-8F illustrate a preferred manner for utilizing the apparatus of the invention.
Figure 8B:
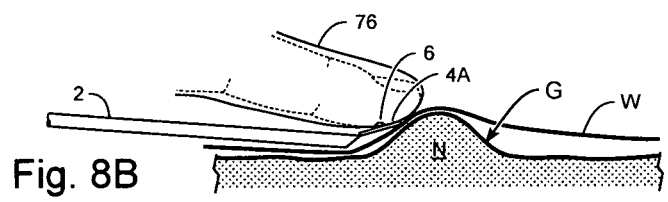
Figure 8C:
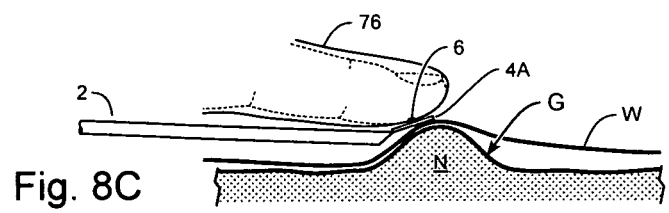
Figure 8D:
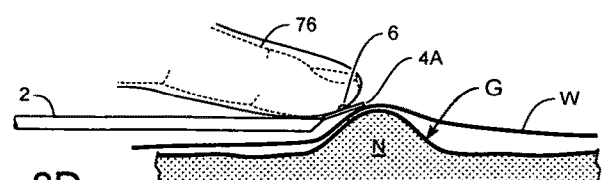
Figure 8E:
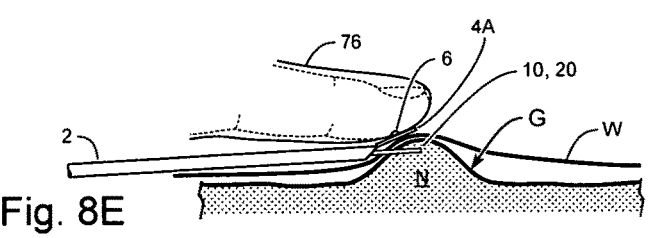

As indicated above, the subject invention is intended to provide protection to the hand of a physician or technician performing a core biopsy procedure on an internal organ, e.g., the prostate gland. Typically, the procedure involves placing the physician's finger into a body cavity for the purpose of palpating the organ of interest to locate suspicious nodules or lesions indicative of cancer or other serious diseases. When a biopsy needle assembly is activated to take a core sample of such suspicious area, the physician's fingertip must be protected from contact with the needle assembly to avoid injury. In addition to providing such protection, the apparatus of the invention serves to more precisely direct the needle assembly along a path to achieve the desired result.

Referring now to the drawings, FIGS. 5-9 show a preferred embodiment of the invention as comprising a tubular housing 2, fabricated from a suitable plastic or metal, that defines an open passageway 2A extending continuously between its proximal and distal ends, 2B and 2C, respectively. Preferably, housing 2 is fabricated from a material that renders it both sterilizeable and disposable after use. Passageway 2A is adapted to receive and guide a conventional biopsy needle assembly BA, e.g., of the cannula/stylet type shown and described with reference to prior art FIGS. 2-4, to the intended site of the biopsy. A suitable needle assembly that is useful with invention is the Max-Core® Disposable Core Biopsy Instrument made by C.R. Bard, Inc. A typical length for the tubular housing 2 is between 6 and 9 inches, and, as illustrated in FIG. 5A, housing 2 has an outer diameter OD of about 3/32, and an inner diameter ID of about 1/16 inch. The physical size of housing 2 will depend upon type of biopsy to be performed, the patient's anatomy, and the dimensions of the biopsy needle assembly to be used.

Mounted in a cantilever fashion at each of the opposing ends of the housing 2 are a pair of rigid flanges 4A and 4B. Preferably, each of these flanges is planar in shape and has a typical width y (shown in FIG. 6) of between about 1/8 and 3/16 inch, and a length x (shown in FIG. 5) of about 3/8 inch. The two flanges extend outwardly relative to the central axis A of passageway 2A at an acute angle, with flange 4A at the distal end of housing 2 extending upwardly in a vertical plane, while flange 4B at the proximal end of housing 2 extending downwardly, in the same vertical plane. Thus, either end the apparatus shown in FIG. 5 can be used to accurately position the sharpened end of the biopsy needle assembly during the biopsy procedure. However, for reasons explained below, it is preferred that the respective acute angles at which the flanges extend from housing 2 differ, whereby one extends outwardly from the housing at an angle of approximately 15 degrees, while the other extends at an angle of approximately 25 degrees. These angles may vary depending of the type of biopsy being performed. Between the opposing ends of the flanges is a flat outer surface 5 having a centrally-located fiducial 6 thereon that is detectable by touch. Preferably, the fiducial is a small bump that protrudes outwardly from surface 5. During use of the apparatus, the up-turned flat surface 5 located at the distal end of housing 2 is engaged by the fingertip of the user. This engagement provides multiple advantages, including, a secure finger placement, shielding of the finger from the biopsy needle, proper orientation of the biopsy needle, a uniform pressure point for the finger, prevention of finger movement during the biopsy procedure, assurance that the needle stays on axis during the biopsy procedure, and resistance to finger overrun of the flange, even at odd angles. The fiducial 6 serves as a means to calibrate, by feel, the placement of the needle tip relative to the intended biopsy site.

While the up-turned flange 4A at the distal end of housing 2 has multiple purposes, the down-turned flange 4B functions to facilitate the loading of the biopsy needle assembly into the passageway 2A. In effect, it provides a ramp that directs the distal end of the needle assembly directly to the passageway opening 2D. (See FIG. 6). Thus, there is a flange mounted at both ends of housing 2, each providing a function depending on which end is in use as the distal end of housing 2 at the time of the biopsy procedure.

Figure 8F:
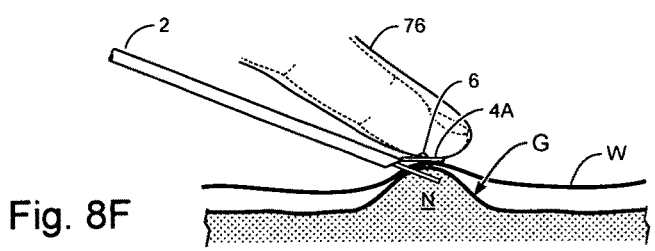

In performing a biopsy of the prostate using the apparatus of FIG. 5, the process illustrated in FIGS. 8A-8F is preferred. As shown in FIG. 8A, the physician or technician will first use a gloved index finger 76 to palpate the prostate gland G to locate an irregularity (e.g., a nodule N) of interest. This process is carried out through the wall W of the rectum. Having located a nodule of interest, the physician will maintain a slight pressure between the palpating fingertip and the irregularity while simultaneous introducing the distal end of housing 2. See FIG. 8B. Note, at this time, the needle assembly is yet to be loaded. Flange 4A slides between the fingertip and nodule, urging the fingertip upwards, shown in FIG. 8C, and allowing final positioning of the distal end of housing 2 in contact with the nodule. See FIG. 8D. At this time the fingertip has moved back to the flat surface 5 of flange 4A, and the underlying fiducial 6 indicates that it is safe to load the biopsy needle assembly into passageway 2A. Fingertip pressure is then applied to the nodule through the flange, and the needle gun is actuated to sequentially advance the stylet and cannula components into the nodule to excise a core sample at a precise location underlying the fiducial. See FIG. 8E. Note, owing to the narrow width of flange 4A, the physician can palpate the nodule while engaging the flange. This further assures the accuracy of the biopsy. The angle at which the needle assembly enters the nodule can be safely varied by increasing the angle of attack between the fingertip and the nodule, as shown in FIG. 8F. By using a double-ended apparatus, as depicted in FIG. 5, where the flanges 4A and 4B extend at different acute angles, the physician can vary the attack angle to achieve a deeper, or shallower core sample by simply selecting one end or the other (of housing 2) for the procedure.

A variation of the apparatus of the invention is depicted in FIG. 9 where the distal end of housing 2 defines a trumpet-shaped opening to facilitate the loading of the needle assembly into passageway 2A.

A preferred method of fabricating housing 2 with integral flanges 4A and 4B from a metal, such as stainless steel, brass, copper or aluminum, is to first cut a tube of the desired metal to a suitable length, e.g. 7 inches. The outer and inner diameters of the tube are as described above. An end of the tube is then placed between the jaws of a vice to a length, measured from the tube end, equal to the desired length of a flange, e.g., ⅜ inch. The vice is then operated to apply a compression force to diametrically opposed surfaces of the tube end, and this force is continued until the walls of the tube move into intimate contact. This flattened region of the tube thus becomes either of the flanges 4A or 4B, which will now be integral with the tube housing 2. Note, this flattened region will have a thickness equal to twice that of the tube wall, as illustrated in FIG. 6. While still engaged in the vice, the tube is then bent to a desired angle, i.e., angle a shown in FIG. 5. As noted above, this angle will be between about 15 to 25 degrees, relative to the flattened end of the tube. A suitable borehole 2D, shown in FIG. 6, is then reamed through the underside of the bent end of the tube, until it smoothly communicates with the tube passageway 2A. The fiducial 6 is then embossed or otherwise formed on the top surface of the flange.

To fabricate the above apparatus from plastic, a suitable plastic tube is cut to a desired length, e.g., 7 inches. One end of the plastic tube is heated to soften its plastic material. While in a softened stated, the opposing walls of the heated end portion of the tube are compressed together until they become fused together; in this manner a plastic flange 4 is formed that is integral with the plastic tube. While still in a softened state, the flange is bent to the desired angle A, and while still in a softened state, a specially configured platen featuring a negative image of fiducial 6 is used to form the fiducial on one of the planar surfaces of the flange. The heated end of the plastic tube is slowly cooled to allow the flange to retain its desired shape and orientation relative to the tube housing 2. After cooling, the apparatus is then bored, as described in the preceding paragraph.

As an alternative to the multiple steps described above, in which case a monolithic plastic apparatus is produced, the flanged ends of the device can be produced by an injection molding process, and these ends can be separately affixed to the end(s) of a plastic tube.

The invention has been described with particular reference to a transrectal biopsy needle used to take core samples of the prostate gland. It will be appreciated, however, that the invention can be used to take core samples from other body cavities, e.g., within the vagina or throat of a patient, or even from tissue underlying external suspicious surface lesions and sores that are readily visible on the outer skin of a patient. Obviously, the physical dimensions and materials of the apparatus described herein may vary in adapting the apparatus for such uses and, thus, should not be considered as limiting.

What is claimed is:

1. An apparatus for biopsying a biological mass that has been palpated by the fingertip of a user, said apparatus comprising;

a housing (2) defining a housing passageway (2A) and extending along a central axis (A) between a proximal end (2B) and a distal end (2C), a cannula (20) defining a cannula passageway and being slidably disposed in said housing passageway (2A), a stylet (10) defining a slot for being slidably disposed in said cannula passageway of said cannula (20) and for sliding outwardly from said distal end (2C) of said housing (2) into the biological mass with a segment of the biological mass expanding into said slot and said slot containing a biopsy of the biological mass when said cannula (20) is slid through said housing passageway (2A) outwardly from said distal end (2C) of said housing (2) to cut the segment of the biological mass, a first flange (4A) extending from said distal end (2C) of said housing (2) at a first acute angle for protecting the fingertip when sliding each of said cannula (20) and said stylet (10) through said housing passageway (2A) outwardly from the distal end (2C) of the housing (2) and retracting back into the housing passageway (2A) with the biopsy of the biological mass being disposed in said slot, characterized by, a distal fiducial (6) protruding upwardly from said first flange (4A) for merely touching by the fingertip of the human to precisely position the fingertip on the biological mass without moving the flange and indicate to the human it is safe to cut the biopsy of the biological mass, a second flange (4B) extending from said proximal end (2B) of said housing (2) at a second acute angle for guiding said cannula (20) and said stylet (10) into said housing passageway (2A), and a proximal fiducial (6) protruding downwardly from said second flange (4B) for detection by the fingertip.

2. An apparatus as set forth in claim 1 wherein said first flange (4A) is arcuate in shape and has a width (y) of between one-eighth an inch (⅛") and three-eighths an inch (⅜").

3. An apparatus as set forth in claim 1 wherein said second flange (4B) is arcuate in shape and has a width (y) of between one-eighth an inch (⅛") and three-eighths an inch (⅜").

4. An apparatus as set forth in claim 1 wherein said first acute angle is between about 10° and about 30°.

5. An apparatus as set forth in claim 1 wherein said second acute angle is between about 10° and about 30°.

6. An apparatus for biopsying a biological mass that has been palpated by the fingertip of a user, said apparatus comprising;

a housing (2) defining a housing passageway (2A) and extending along a central axis (A) between a proximal end (2B) and a distal end (2C), a cannula (20) defining a cannula passageway and being slidably disposed in said housing passageway (2A), a stylet (10) defining a slot for being slidably disposed in said cannula passageway of said cannula (20) and for sliding outwardly from said distal end (2C) of said housing (2) into the biological mass with a segment of the biological mass expanding into said slot and said slot containing a biopsy of the biological mass when said cannula (20) is slid through said housing passageway (2A) outwardly from said distal end (2C) of said housing (2) to cut the segment of the biological mass, a first flange (4A) extending from said distal end (2C) of said housing (2) at a first acute angle for protecting the fingertip when sliding each of said cannula (20) and said stylet (10) through said housing passageway (2A) outwardly from the distal end (2C) of the housing (2) and retracting back into the housing passageway (2A) with the biopsy of the biological mass being disposed in said slot, characterized by, a distal fiducial (6) protruding upwardly from said first flange (4A) for merely touching by the fingertip of the human to precisely position the fingertip on the biological mass without moving the flange and indicate to the human it is safe to cut the biopsy of the biological mass, a second flange (4B) extending from said proximal end (2B) of said housing (2) at a second acute angle for guiding said cannula (20) and said stylet (10) into said housing passageway (2A), and said first acute angle being different from said second acute angle.

7. An apparatus as set forth in claim 6 wherein said first acute angle is of about 15° and said second acute angle is of about 25°.

8. An apparatus as set forth in claim 6 wherein said first acute angle is of about 25° and said second acute angle is of about 15°.

9. An apparatus for biopsying a biological mass that has been palpated by the fingertip of a user, said apparatus comprising;

a housing (2) of a cylindrical shape defining a housing passageway (2A) and extending along a central axis (A) between a proximal end (2B) and a distal end (2C), a cannula (20) of a cylindrical shape extending between ends and defining a cannula passageway and being slidably disposed in said housing passageway (2A), said cannula (20) including a sharpened end having a crescent shape as viewed in cross section to define a point and curving from said point to define said sharpened end, said distal end (2C) of said housing (2) being at an acute angle to said central axis (A) for disposing said sharpened end of said cannula (20) generally parallel to said distal end (20) of said housing (2), a stylet (10) of a cylindrical shape having a pointed end and defining a slot of a rectangular shape spaced from said pointed end for being slidably disposed in said cannula passageway of said cannula (20) and for sliding outwardly from said distal end (2C) of said housing (2) with said pointed end puncturing into the biological mass with a segment of the biological mass expanding into said slot and said slot containing a biopsy of the biological mass when said cannula (20) is slid through said housing passageway (2A) outwardly from said distal end (2C) of said housing (2) to cut the segment of the biological mass, and a first flange (4A) extending outwardly and upwardly from said distal end (2C) of said housing (2) at a first acute angle for protecting the fingertip when sliding each of said cannula (20) and said stylet (10) through said housing passageway (2A) outwardly from said distal end (2C) of said housing (2) and retracting back into said housing passageway (2A) with the biopsy of the biological mass, a second flange (4B) extending outwardly and downward from said proximal end (2B) of said housing (2) at a second acute angle for guiding said cannula (20) and said stylet (10) into said housing passageway (2A), characterized by, a distal fiducial (6) of a spherical shape protruding upwardly from said first flange (4A) for touching by the fingertip of the human to precisely position the fingertip on the biological mass and indicate to the human it is safe to cut the biopsy of the biological mass, a proximal fiducial (6) of a spherical shape protruding downwardly from said second flange (4B) for touching by the fingertip of the human to precisely position the fingertip on the biological mass and indicate to the human it is safe to cut the biopsy of the biological mass, said flanges (4A, 4B) being arcuate in shape and having a width (y) of between one-eighth (⅛") and three-eighths (⅜"), said first acute angle being different from said second acute angle, and each of said angles being between about 10° and about 30°.

\* \* \* \* \*